(12) United States Patent
Durr et al.

(10) Patent No.: US 12,203,924 B2
(45) Date of Patent: Jan. 21, 2025

(54) OFFSET ILLUMINATION CAPILLAROSCOPE

(71) Applicant: THE JOHNS HOPKINS UNIVERSITY, Baltimore, MD (US)

(72) Inventors: Nicholas James Durr, Baltimore, MD (US); Gregory N. Mckay, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 276 days.

(21) Appl. No.: 17/770,890

(22) PCT Filed: Oct. 22, 2020

(86) PCT No.: PCT/US2020/056879
§ 371 (c)(1),
(2) Date: Apr. 21, 2022

(87) PCT Pub. No.: WO2021/081215
PCT Pub. Date: Apr. 29, 2021

(65) Prior Publication Data
US 2022/0381763 A1    Dec. 1, 2022

Related U.S. Application Data

(60) Provisional application No. 62/924,986, filed on Oct. 23, 2019.

(51) Int. Cl.
*G01N 33/49* (2006.01)
*G01N 15/10* (2006.01)
(Continued)

(52) U.S. Cl.
CPC ............. *G01N 33/49* (2013.01); *G01N 15/10* (2013.01); *G01N 15/1433* (2024.01); *G01N 2015/016* (2024.01)

(58) Field of Classification Search
CPC . A61B 5/0075; A61B 5/02055; A61B 5/1455; G01N 15/10; G01N 2015/1486;
(Continued)

(56) References Cited

U.S. PATENT DOCUMENTS

2007/0070328 A1\* 3/2007 Rensen ................ A61B 5/0068
600/317
2009/0122299 A1\* 5/2009 Zalevsky .............. G01J 3/0218
356/600
(Continued)

FOREIGN PATENT DOCUMENTS

EP         3716207 A1    9/2020
JP      2007524075 A    8/2007
(Continued)

OTHER PUBLICATIONS

Gentil, T., Extended European Search Report in corresponding International Application No. PCT/US2020/056879 mailed on Mar. 3, 2023, 8 pages.
D. Khranilova, International Search Report and Written Opinion in corresponding International Application No. PCT/US2020/056879 mailed on Feb. 4, 2021, 6 pages.

*Primary Examiner* — Tri T Ton
(74) *Attorney, Agent, or Firm* — MH2 Technology Law Group LLP

(57) ABSTRACT

Techniques for label-free determination of a value of at least one blood property are presented. The techniques may utilize a device that includes an optical objective including at least one lens, at least a first light source situated so as to provide light to a body part at a location that is off-center from a central axis of the objective, at least a first electronic detector situated to receive light gathered by the optical objective and generate image data, at least one electronic processor communicatively coupled to the first electronic detector, the at least one electronic processor configured to determine the value of the at least one blood property based at least in part on the image data, and an output interface
(Continued)

communicatively coupled to the at least one electronic processor and configured to provide the value of the at least one blood property.

40 Claims, 16 Drawing Sheets

(51) Int. Cl.
*G01N 15/1433* (2024.01)
*G01N 15/01* (2024.01)

(58) Field of Classification Search
CPC ........... G01N 2015/1488; G01N 33/49; G01N 15/01; G01N 15/1433; G01N 2015/016; G06T 2207/30104
See application file for complete search history.

(56) References Cited

U.S. PATENT DOCUMENTS

| | | | |
|---|---|---|---|
| 2014/0249429 A1 | 9/2014 | Tran | |
| 2015/0359440 A1 | 12/2015 | Kvernebo | |
| 2018/0214009 A1* | 8/2018 | Endo | A61B 1/063 |
| 2019/0320246 A1 | 10/2019 | Aumer et al. | |
| 2019/0392953 A1* | 12/2019 | Steuer | G16H 40/67 |
| 2020/0126664 A1* | 4/2020 | Sato | G16H 50/20 |

FOREIGN PATENT DOCUMENTS

| | | |
|---|---|---|
| RU | 2367340 C2 | 9/2009 |
| WO | 2009039466 A1 | 3/2009 |

\* cited by examiner

Scale bars are 10μm.

OFFSET ILLUMINATION CAPILLAROSCOPE

CROSS-REFERENCE TO RELATED APPLICATIONS

The present application is the national stage entry of International Patent Application No. PCT/US2020/056879, filed on Oct. 22, 2020, and published as WO 2021/081215 A1 on Apr. 29, 2021, which claims the benefit of priority of U.S. Provisional Application No. 62/924,986, filed on Oct. 23, 2019, all of which are hereby incorporated by reference herein in their entireties.

FIELD

This disclosure relates generally to blood testing.

BACKGROUND

Blood tests such as complete blood counts ("CBC") generally require invasive blood draws. While blood draws are generally low-risk, invasive procedures such as blood draws for CBC tests have certain disadvantages. For example, repetitive blood draws commonly leads to anemia in neonates. Thus, current protocols limit the temporal frequency at which such tests can be administered. Further, blood draws require trained personnel (e.g., a phlebotomist and a lab technician). Expensive laboratory equipment is required for CBC blood draws and analysis, limiting access in remote and low-resource settings. Yet further, hemolysis of blood cells ex vivo is common as samples age. Still further, blood draws generally require patients to visit a hospital or other care facility, subjecting them to nosocomial infection. Thus, invasive blood draws are inferior to non-invasive procedures that can achieve the same or equivalent results.

SUMMARY

According to various embodiments, a system for label-free determination of a value of at least one blood property is disclosed. The system includes: an optical objective comprising at least one lens; at least a first light source situated so as to provide light to a body part at a location that is off-center from a central axis of the objective; at least a first electronic detector situated to receive light gathered by the optical objective and generate image data; at least one electronic processor communicatively coupled to the first electronic detector, the at least one electronic processor configured to determine the value of the at least one blood property based at least in part on the image data; and an output interface communicatively coupled to the at least one electronic processor and configured to provide the value of the at least one blood property.

Various optional features of the above embodiments include the following. The system may further include a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror. The at least one blood property may include a rate of change of a quantifiable blood property. The at least one blood property may comprise a count of, or ratio comprising, of at least one of: red blood cells, platelets, lymphocytes, neutrophils, lymphocytes, monocytes, eosinophils, or basophils. The at least one blood property may include at least one of: heart rate or blood oxygenation. The system may further include a machine learning classifier trained to identify in the digital image at least one of: red blood cells, platelets, lymphocytes, neutrophils, lymphocytes, monocytes, eosinophils, or basophils. The body part may include a lingual frenulum. The at least a first light source may be situated to provide light to the body part through the objective. The system may further include an annulus comprising at least two vacuum interfaces configured to adhere the annulus to a body part using at least one air pressure differential, wherein the optical objective is situated so as to gather light from the body part through a central opening of the annulus. The system may further include a temperature sensor situated on the annulus and communicatively coupled to the at least one electronic processor, wherein the at least one electronic processor is further configured to determine a temperature from a signal received from the temperature sensor. The at least two vacuum interfaces may be configured to adjust a lateral position of the annulus on the body part by applying different air pressure differentials to different vacuum interfaces.

According to various embodiments, a method of label-free determination of a value of at least one blood property is disclosed. The method includes: applying a device to a body part of a patient, the device comprising: an optical objective comprising at least one lens; at least a first light source situated so as to provide light to the body part at a location that is off-center from a central axis of the objective; at least a first electronic detector situated to receive light gathered by the optical objective and generate image data; at least one electronic processor communicatively coupled to the first electronic detector, the at least one electronic processor configured to determine the value of the at least one blood property based at least in part on the image data; and an output interface communicatively coupled to the at least one electronic processor and configured to provide the value of the at least one blood property; and obtaining a reading from the output interface, the reading indicating the value of the at least one blood property.

Various optional features of the above embodiments include the following. The device may further include a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror. The at least one blood property may include a rate of change of a quantifiable blood property. The at least one blood property may include a count of, or ratio comprising, of at least one of: red blood cells, platelets, lymphocytes, neutrophils, lymphocytes, monocytes, eosinophils, or basophils. The at least one blood property may include at least one of: heart rate or blood oxygenation. The device may further include a machine learning classifier trained to identify in the digital image at least one of: red blood cells, platelets, lymphocytes, neutrophils, lymphocytes, monocytes, eosinophils, or basophils. The body part may include a lingual frenulum. The at least a first light source may be situated to provide light to the body part through the objective. The device may further include comprising an annulus comprising at least two vacuum interfaces configured to adhere the annulus to a body part using at least one air pressure differential, wherein the optical objective is situated so as to gather light from the body part through a central opening of the annulus. The device may further include a temperature sensor situated on the annulus and communicatively coupled to the at least one electronic processor, wherein the at least one electronic processor is further configured to determine a temperature from a signal received from the temperature sensor. The at least two vacuum interfaces may be configured to adjust a lateral position of the annulus on the body part by applying different air pressure differentials to different vacuum interfaces.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Figure 1:
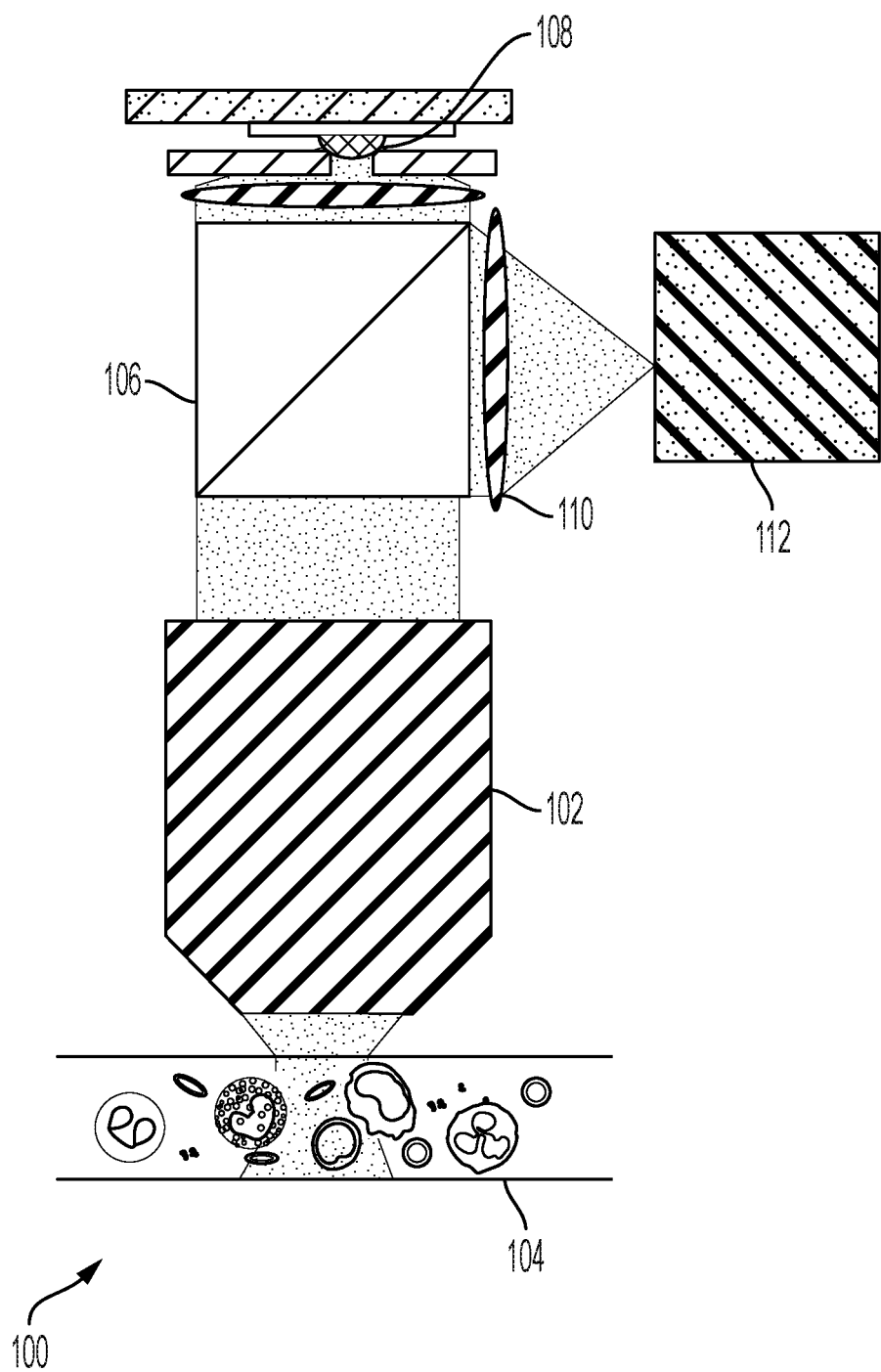
FIG. 1 is a schematic diagram of a single light source system for label-free determination of a value of at least one blood property according to various embodiments.

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Some embodiments provide for non-invasive blood testing, providing an absolute or relative count of any of a variety of blood cells. Such embodiments may image, characterize, and count blood cells in vivo, non-invasively, using high-speed, label-free intravital microscopy in a human body part such a lingual frenulum or other mucosal tissue. Here, "label-free" indicates that contrast, fluorescent, or other dye agents are not required. Some embodiments provide label-free imaging using hemoglobin's absorption spectrum for red blood cell contrast, and measure backscattering, size, morphology, and granularity to determine platelet and white blood cell types.

Some embodiments utilize structured illumination using light emitting diodes or other light sources to generate optimal contrast. In particular, some embodiments utilize one or more light sources that are off-center from a central axis of the optical objective used to gather light from the human body part. Some embodiments utilize one off-center light source, a single optical objective, and a single detector for simultaneous phase and absorption contrast. Other embodiments utilize two off-center light sources, a single optical objective, and two-detector gradient back-illumination for isolating phase and absorption contrast. In some embodiments, the offset of illumination and detection axes produces a gradient of intensity across the field of view, and results in phase contrast due to the net oblique illumination. Some embodiments exploit the detection of differential back and side scattering for blood particle identification.

Some embodiments use relatively inexpensive cameras and do not require optical benches or vibration dampening techniques as required by the prior art. For example, some embodiments temporarily adhere to the human body part in which blood is being imaged by way of differential air pressure. Such embodiments may utilize inexpensive cameras that capture images at a rate of 100-200 Hz with sub-50 millisecond exposure times. Some embodiments utilize cameras with sub two-millisecond exposure times. Other embodiments may use slower cameras, e.g., cameras that capture images at a rate of 30 frames per second. Some embodiments may obtain images using a smart phone camera.

Some embodiments include further useful features. For example, some embodiments may be hand-held devices, usable by medical technicians. The form factor may be similar to a thermometer. Some embodiments may utilize a vacuum-based optical objective housing to stabilize the field of view on a capillary and to maintain a precise and stable location in three-dimensional space relative to the human body part for imaging. Some embodiments provide transillumination geometry for lingual frenula and/or other mucosal tissue. Some embodiments utilize a high-speed tunable lens to optimize focus. Some embodiments include a temperature probe in the optical objective housing for ventral tongue temperature determination. Some embodiments may measure any, or a combination, of temperature, heart rate, and blood oxygenation.

These and other features and embodiments are presented herein in detail.

FIG. 1 is a schematic diagram of a single light source system 100 for label-free determination of a value of at least one blood property according to various embodiments. System 100 may be implemented as a hand-held device according to some embodiments.

System 100 includes light source 108, which may include a light emitting diode ("LED") or other light source. The wavelength of the light source 108 may be selected to be infrared (e.g., 900 nm) which tends to pass through flesh well, or visible blue-green (e.g., 520 nm) which tends to absorb well by red blood cells. System 100 also includes optical objective 102, which may be a microscope objective. Light source 108 is positioned so as to direct light through beam splitter 106 to optical objective 102 at a location that is off-center from a central axis of optical objective 102. The amount of offset may be selected as described below in reference to FIG. 3. According to some embodiments, the usage of one or more relatively small, relatively bright, off-axis light sources provides homogeneous oblique illumination of capillary 104 and the blood cells therein. Alternatively, the light source 108 can be imaged on-axis into the tissue, and the imaging sensor 112 can be offset to produce phase contrast.

Light from light source 108 thus directs light to beam splitter 106. Beam splitter 106, which may include a half-silvered mirror, passes about half of the light originating from light source 108 through optical objective 102 to capillary 104. In turn, light scattered by capillary 104 and gathered by optical objective 102 is passed back to beam splitter 106, which reflects about half of such light through focusing optics 110 to imaging sensor 112.

Imaging sensor 112 may be or include a metal-oxide semiconductor ("MOS") device, such as a complimentary MOS ("CMOS") device or charge coupled device ("CCD"). According to some embodiments, imaging sensor 112 may have an image capture rate of 100-200 Hz with sub-50 millisecond (e.g., sub two-millisecond) exposure times. According to some embodiments, imaging sensor 112 may have an image capture rate of 30 frames per second. Some embodiments may obtain or illuminate images using a smart phone camera. Imaging sensor 112 may capture single images or video sequences according to various embodiments. Such images may be based on absorption contrast, which may be used for detecting red blood cells, and/or phase contrast, which may be used to profile and determine boundaries (e.g., membranes) and subcellular components (e.g., organelles) of white blood cells. Offset illumination, as disclosed herein, is particularly useful for phase contrast.

Imaging sensor 112 is coupled to at least one electronic processor, which may include one or more Graphical Processing Units ("GPU"). The electronic processor perform image processing as disclosed herein.

Figure 2:
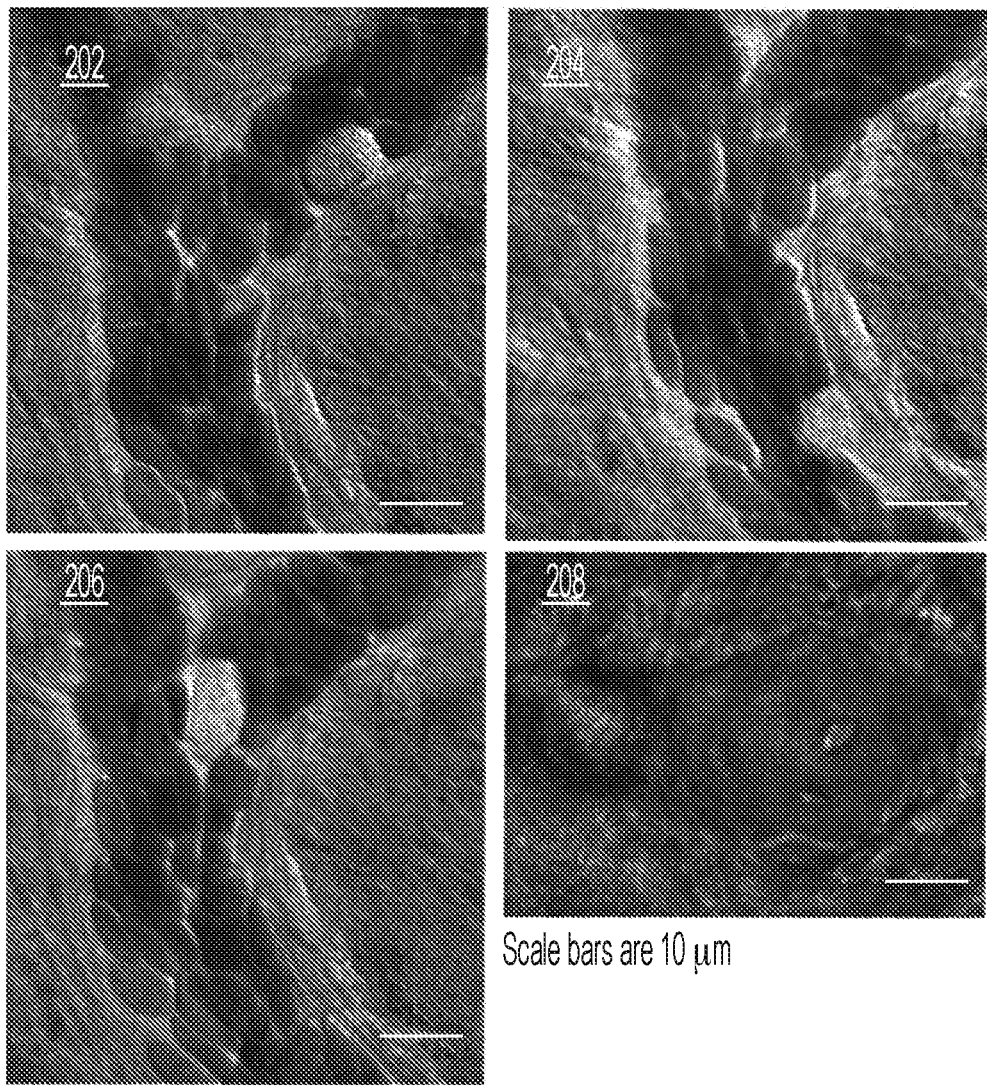
FIG. 2 illustrates various blood cell types according to various embodiments.

FIG. 2 illustrates various blood cell types according to various embodiments. In particular, FIG. 2 depicts example blood cell types capable of being imaged and counted by embodiments such as system 100 of FIG. 1. As shown, FIG. 2 depicts granulocytes 202, lymphocytes 204, monocytes 206, and platelets 208.

Embodiments as disclosed herein may utilize machine learning to obtain one or more blood cell counts for one or more blood cell types based on images captured by systems as disclosed herein. Such machine learning may be implemented as described presently. Any of a variety of machine learning algorithms may be used, including but not limited to convolutional neural networks and support vector machines. Machine learning may include a training phase and a usage phase.

For the training phase, physical microfluidic models may be constructed, and one or more blood cell types may be passed through artificial capillaries. This may be imaged, using an embodiment, and the cells manually segmented, e.g., using a mask. (Segmentation here means identifying cell boundaries and/or identifying discrete cells.) The manual segmentations may be used to train a first machine learning classifier, configured to segment cells. Next, the segmented cells may be manually classified (e.g., into red blood cells, platelets, lymphocytes, neutrophils, lymphocytes, monocytes, eosinophils, and basophils) and counted. The manual classifications may be used to train a second machine learning classifier, configured to classify cells.

The count for a still image may be converted to a standard count based on a measured flow rate. That is, the microfluidic model may have artificial capillaries with a circular cross-section and known inner diameter. The standard count may be computed as the product of the number of counted cells in the still image, the cross sectional area of the artificial capillary, the velocity of the blood, and the amount of time corresponding to a known fluidic volume passing through the cross-section. Note that pure blood cells of a single type may be sent through the microfluidic model, such that the initial manual classification may be omitted.

Alternately, instead of, or along with, a physical microfluidic model, a computational forward model may be used for the training phase, where cell sizes and geometry are specified and synthetic images are obtained. Such a forward model may be implemented in the Fourier domain. A circular mask may be simulated, to model a camera's optical objective. Gradient back-illumination can be simulated with Monte Carlo or other light transport models. First and second machine learning classifiers may be developed as described above with respect to the microfluidic model.

For the usage phase, the first and second trained classifiers may be applied to images obtained according to various embodiments disclosed herein, in order to obtain cell identifications and counts for still images. Such counts may be converted to standard counts using an analogous technique to that described above for the microfluidic model, where the patient's capillaries may be assumed to have a circular cross-section for purposes of estimation. The above-described product then yields a standardized cell count, for each of a variety of blood cell types.

Figure 3:
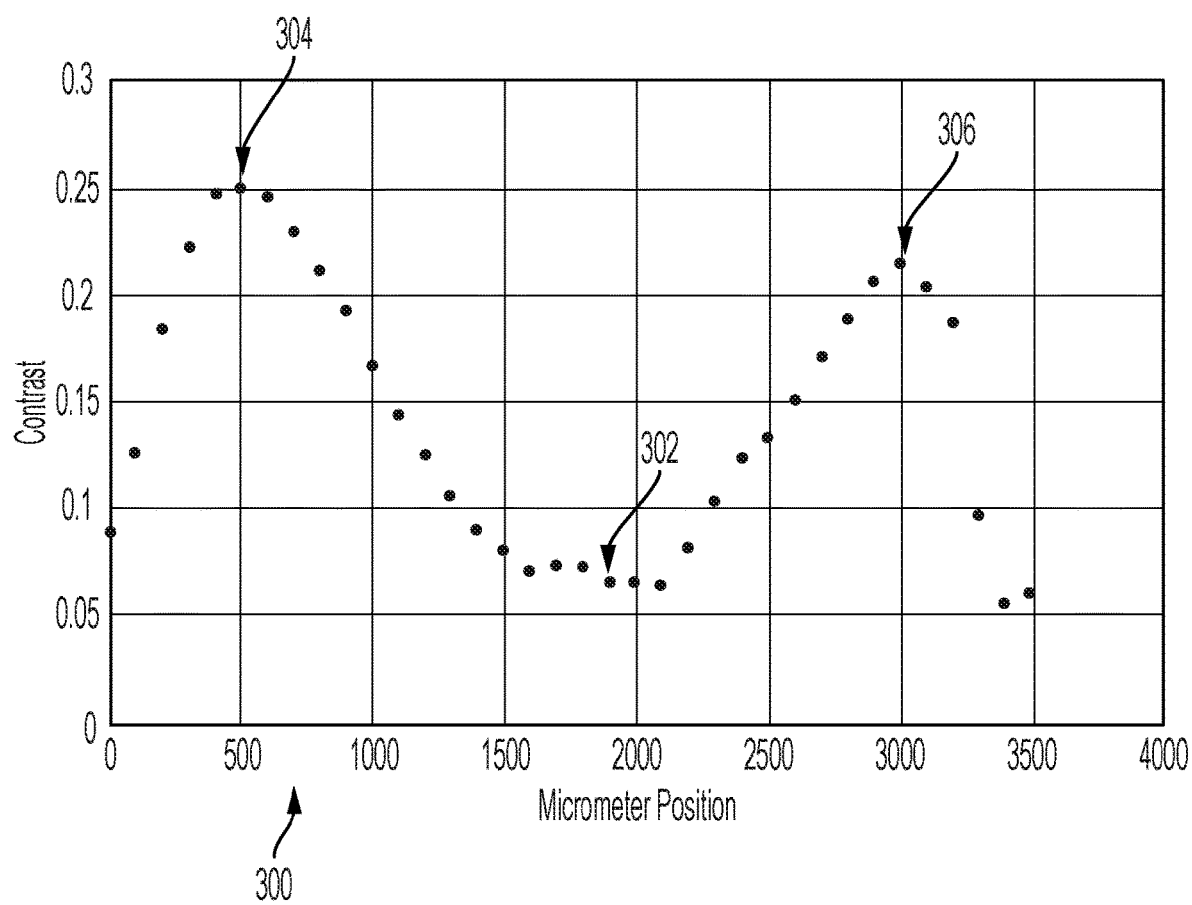
FIG. 3 a graph illustrating contrast optimization with offset light according to various embodiments.
Figure 4:
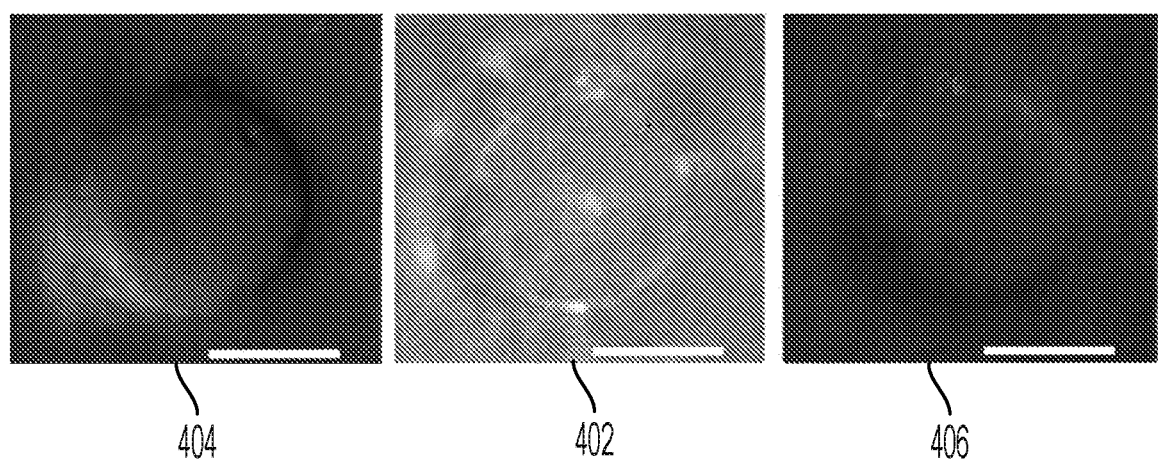
FIG. 4 depicts images captured according to various light source offsets according to various embodiments.

FIG. 3 a graph 300 illustrating contrast optimization with offset light according to various embodiments. In graph 300, the x-axis represents offset in units of mm and the y-axis represents Michelson contrast (unitless). In general, off-axis, pinhole illumination and back scattering produce enhanced phase contrast to weakly scattering particles. Some embodiments exploit this phenomenon to obtain enhanced contrast images. As shown, contrast is low on axis 302. Off axis, at 304 (about 1400 μm to the left of center) and 306 (about 1100 μm to the right of center), contrast is enhanced. FIG. 4 depicts images captured at positions 302, 304, and 306 according to some embodiments.

FIG. 4 depicts images captured using various light source offsets according to various embodiments. In particular, image 402 was captured by an optical microscope using on-axis illumination, e.g., on axis 302 of FIG. 3. Images 404 and 406 were captured by the optical microscope using off-axis illumination, e.g., off axis 304 and 306. As is clear from the images, shape and contrast are greatly enhanced through the use of off-axis illumination.

Figure 5:
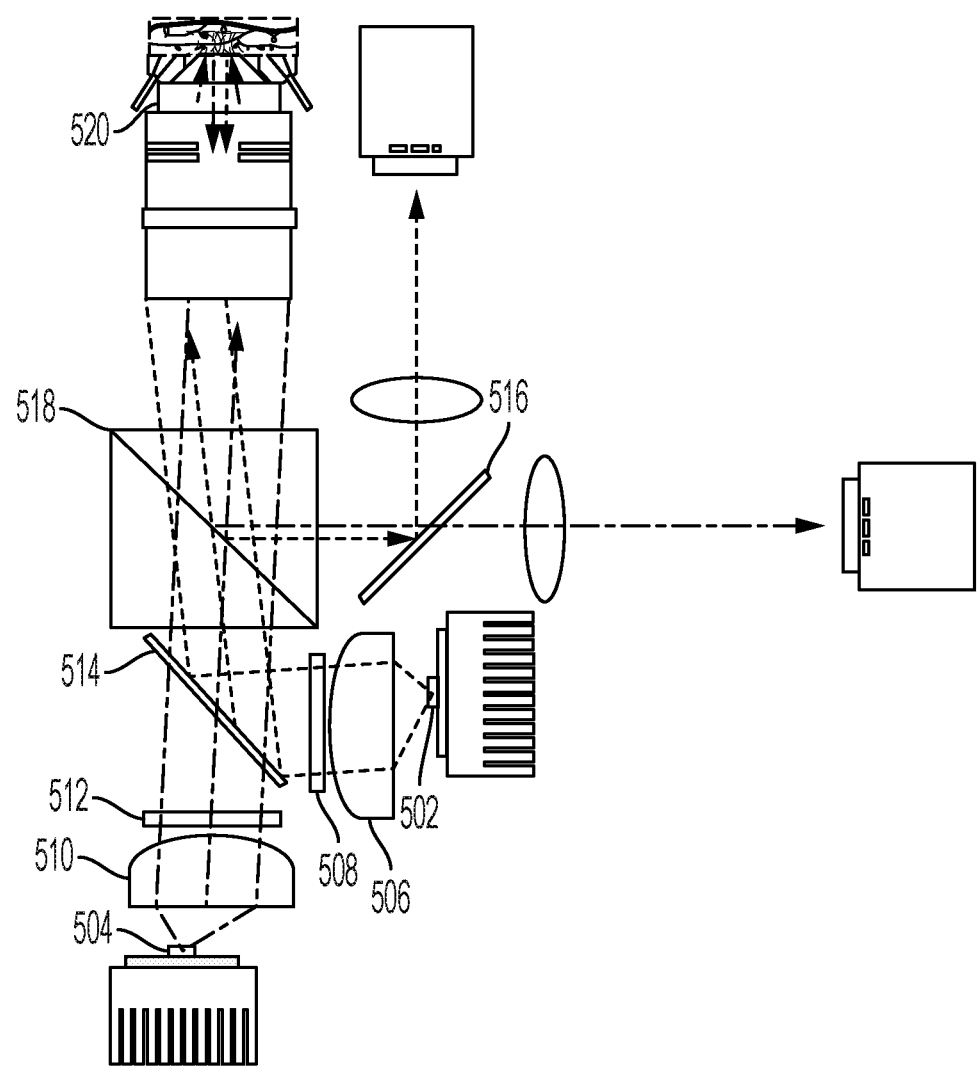
FIG. 5 is a schematic diagram of a dual light source system for label-free determination of a value of at least one blood property according to various embodiments.

FIG. 5 is a schematic diagram of a dual light source system for label-free determination of a value of at least one blood property according to various embodiments.

The system of FIG. 5 includes cyan-color light source 502 and lime-color light source 504. The wavelengths of light sources 502, 504 are selected so as to be sufficiently far apart that the light beams they produce, respectively, may be separated by a dichroic mirror, such as dichroic mirrors 514, 516. Thus, light sources 502, 504 are situated so as to direct their respective beams through respective focusing optics 506, 510 and respective filters 508, 512, to dichroic mirror 514, which collimates them and directs them to beam splitter 518. Beam splitter 518 directs the collimated beams to optical objective 520, which passes the beams to a body part, such as a lingual frenulum or other mucosal surface. Note that the beams arrive at the body part off-center from the central axis of optical objective 520. The beams may be directed to opposite sides of the central axis according to some embodiments.

Light scattered from the body part is gathered by optical objective 520, which passes it back through beam splitter 518 and a tunable lens to dichroic mirror 516. Tunable lens may be a high-speed tunable lens, such as those available from OPTOTUNE of Dietikon, Switzerland. Dichroic mirror 516 splits the light based on its wavelengths, passing lime wavelength light to imaging sensor 516 and reflecting the cyan wavelength light to imaging sensor 518. Imaging sensors 516, 518 may be as shown and described above with respect to imaging sensor 112 of FIG. 1.

Figure 6:
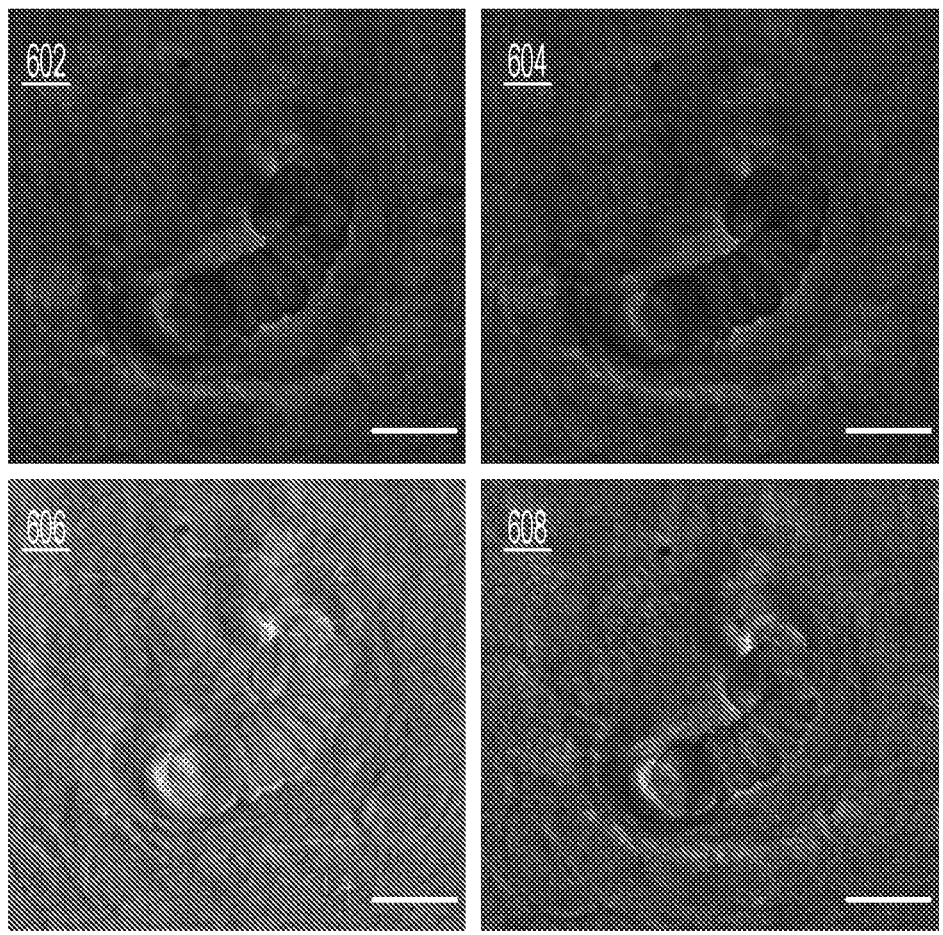
FIG. 6 illustrates various images captured by the system of FIG. 5 according to various embodiments.

FIG. 6 illustrates various images captured by the system of FIG. 5 according to various embodiments. In particular, FIG. 5 depicts an image 602 acquired using only a first light source, an image 604 acquired using only a second light source, a scattering-only image 606 (i.e., phase only image) acquired using both light sources, and an absorption-only image 608 acquired using both light sources. The first light source may be light source 502 of the system of FIG. 5 and the second light source may be light source 504 of the system of FIG. 5. The oblique back-illumination microscopy ("OBM") technique of addition and subtraction may be used to generate absorption-only image 608 and scattering-only image 606. Note that the absorption-only image 608 depicts red blood cells as partial shadows, showing contrast from the difference of the light that is absorbed going through red blood cells versus the light that passes through the less-absorbing surrounding tissue. According to various embodiments, absorption-only and phase-only images may be combined into a single image, e.g., using a different color for each constituent image and overlaying them.

Figure 7:
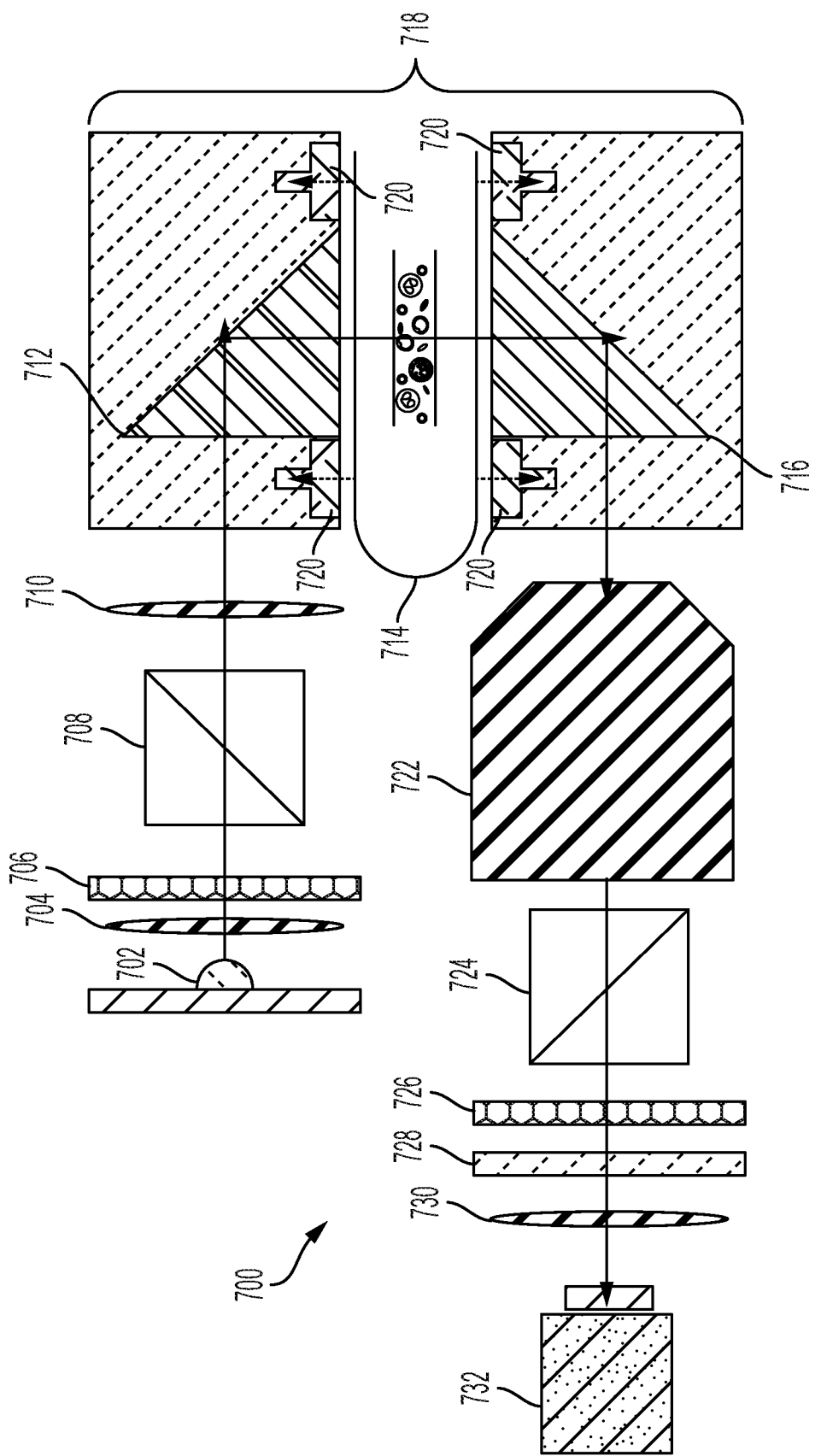
FIG. 7 is a schematic diagram of a single transmission light source intra-frenulum system for label-free determination of a value of at least one blood property according to various embodiments.

FIG. 7 is a schematic diagram of a single transmission light source intra-frenulum system 700 for label-free determination of a value of at least one blood property according to various embodiments. System 700 may be used to image intra-frenulum capillary blood cells, or blood cells in capillaries in other mucosal tissue surfaces. Further, system 700 may exploit differential interference contrast ("DIC") or other transmission phase contrast techniques in order to image phase contrast, as described below.

System 700 includes light source 702, which may be an LED or other light source. Light source 704 directs light through focusing optics 704 and linear polarizer 706 to Wollaston prism 708. Wollaston prism 708 deflects light based on polarization, providing a slight separation into multiple beam portions. Such beam portions are directed through focusing optics 710 to apparatus 718.

Apparatus 718 may be formed as fixed or adjustable separated parallel surfaces, into which a body part such as a lingual frenulum may be inserted. For adjustable embodiments, the distance between such surfaces may be adjusted on-the-fly, as the system is being used. Apparatus 718 includes vacuum interfaces 720, which provide a differential pressure to adhere to the body part through suction. Light entering apparatus 718 is directed by prism 712 through body part 714, such as a lingual frenulum, and capillaries therein. Light exiting body part 714 is directed by prism 716 to optical objective 722. Optical objective 722 gathers such light and passes it to Wollaston prism 724. Wollaston prism 724 recombines the multiple beam portions generated by Wollaston prism 708 in a manner that makes the different phases of the multiple beam portions apparent due to optical wave interference, both additive and subtractive.

The recombined light is then directed to compensator 726, such as a quarter-wave, full-wave, or de Senarmont compensator. From there, the recombined light passes through analyzer 728 to tunable tube lens 730, and finally to imaging sensor 732. The analyzer can be a second linear polarizer oriented perpendicular to linear polarizer 706. Imaging sensor 732 may be as shown and described above with respect to imaging sensor 112 of FIG. 1.

Figure 8:
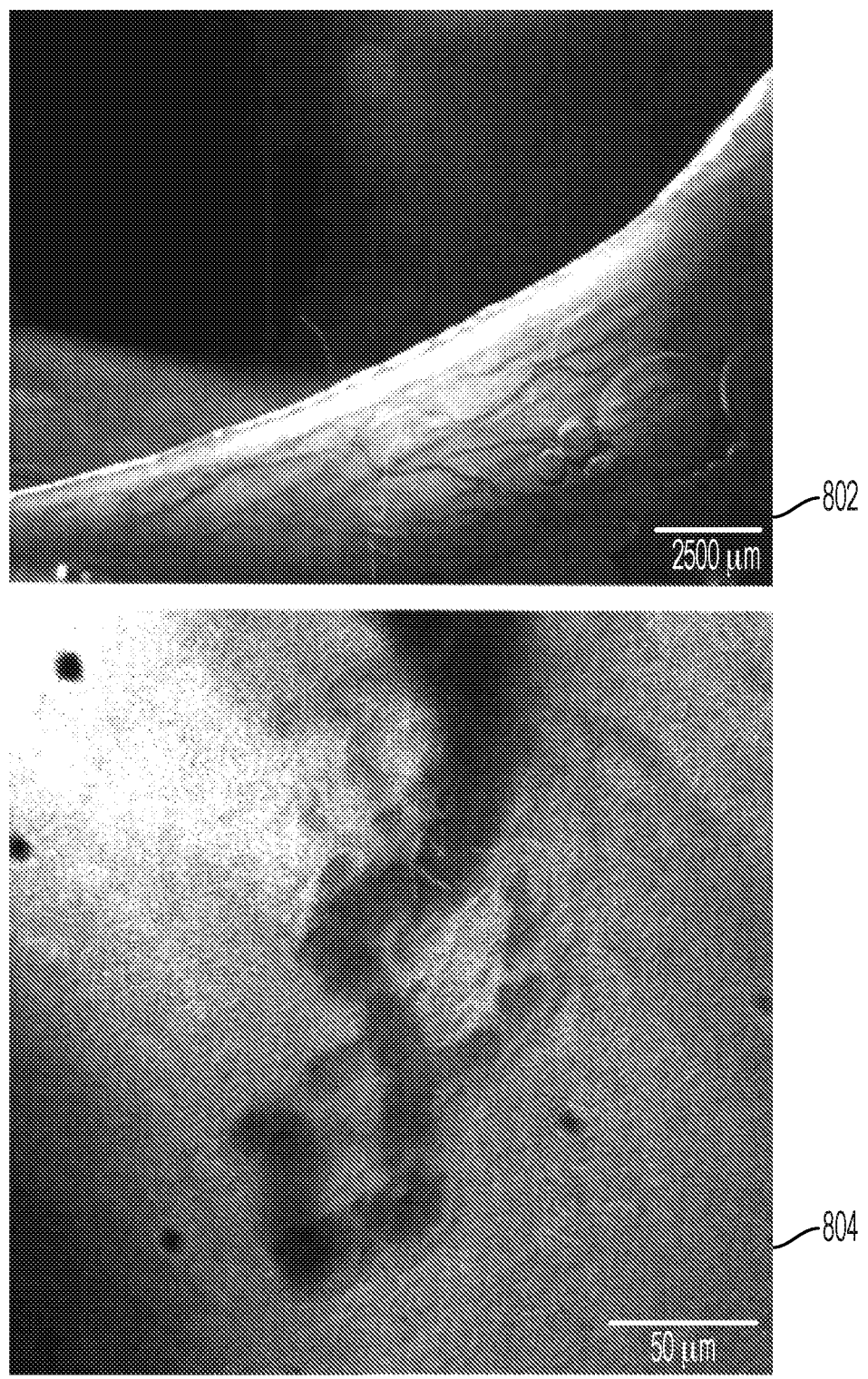
FIG. 8 depicts two images of a lingual frenulum according to various embodiments.

FIG. 8 depicts two images of a lingual frenulum according to various embodiments. in particular, image 802 is a macroscopic vie of a lingual frenulum, and image 804 is a microscopic view of a lingual frenulum. Image 802, which shows capillaries and individual blood cells therein, may be captured using system 700 as shown and described above in reference to FIG. 7.

Figure 9:
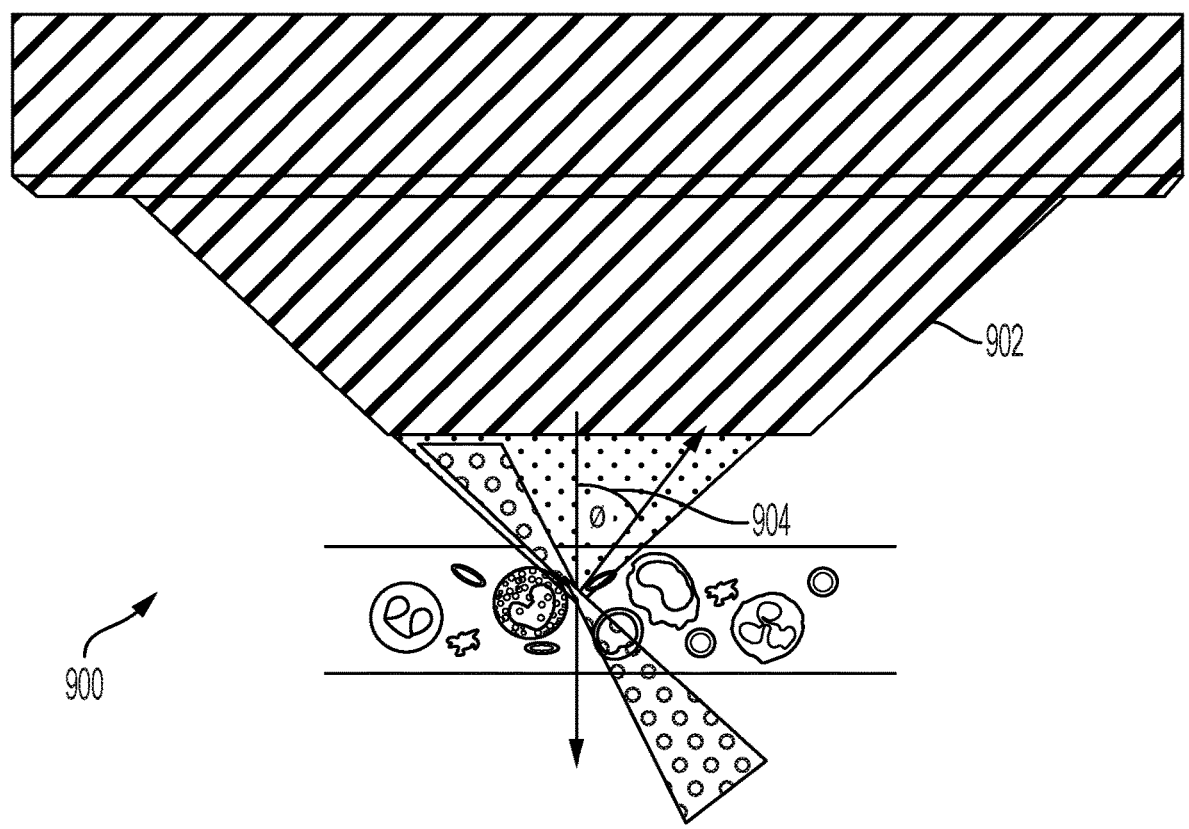
FIG. 9 depicts a system including an optical objective for differential angular scattering using a through-objective light source according to various embodiments.

FIG. 9 depicts a system 900 including an optical objective 902 for differential angular scattering using a through-objective light source according to various embodiments. System 900 may be implemented in a system such as a system 100 of FIG. 1, with optical objective 102 replaced by optical objective 902. Further, an intra-objective light source may be implemented to direct light through optical objective 902. Light scattered by blood cells is detected, and the scattering angle 904 (i.e., the angle between a central axis of optical objective 902 and the scattered light) is determined. Based on the scattering angle 904, different types of white blood cells may be distinguished and identified, as shown and described below in reference to FIG. 10.

Figure 10:
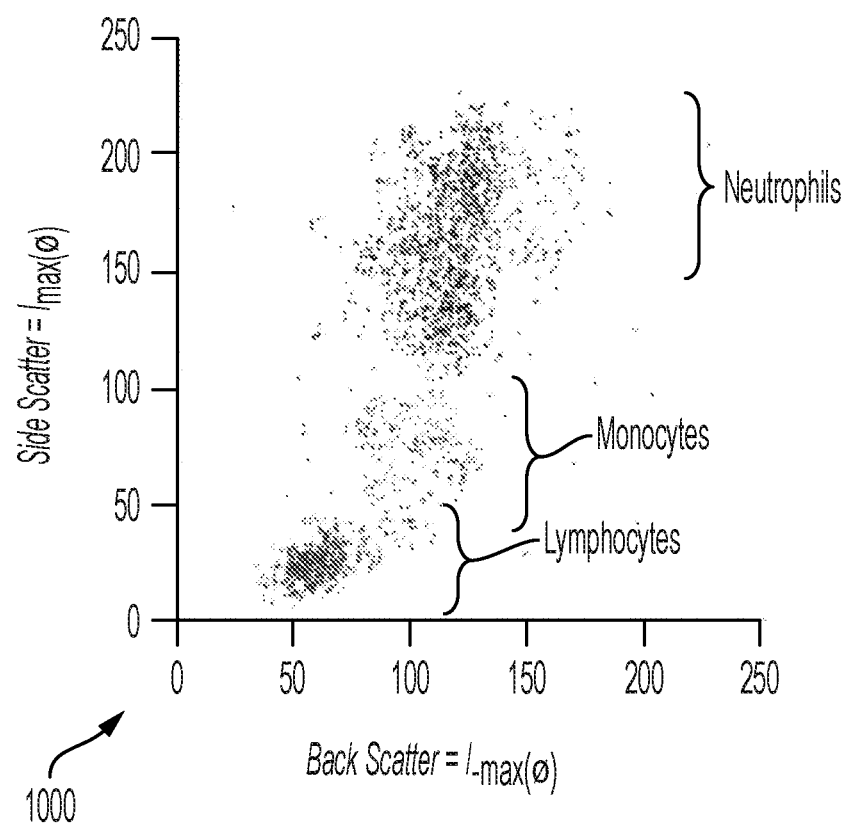
FIG. 10 is a graph of back scatter versus side scatter properties of various white blood cell types according to various embodiments.

FIG. 10 is a graph 1000 of back scatter versus side scatter properties of various white blood cell types according to various embodiments. The x-axis of graph 1000 represents a measure of back scatter in terms of the intensity of light (pixel counts) reflecting back in the direction of incident light, and the y-axis depicts side scatter in terms of the intensity of light scattered (pixel counts) at an angle nearly perpendicular to the incident light. As shown, different white blood cell types have different scattering properties. Neutrophils tend to have higher side scatter than monocytes and lymphocytes. Lymphocytes tend to have lower side scatter and back scatter than monocytes or neutrophils. And monocytes tend to have intermediate side and back scatter in comparison to neutrophils and lymphocytes. Based on these scattering properties, some embodiments may detect and classify various kinds of white blood cells.

Figure 11:
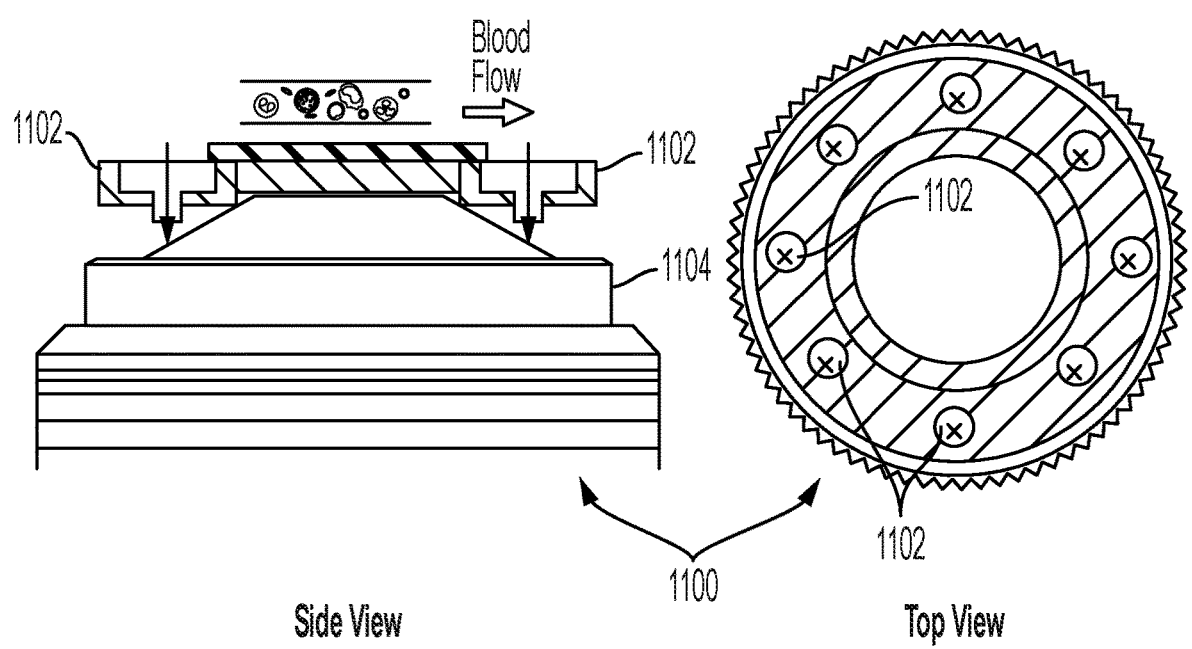
FIG. 11 depicts a vacuum stabilization apparatus for a device for label-free determination of a value of at least one blood property according to various embodiments.

FIG. 11 depicts a vacuum stabilization apparatus 1100 for a device for label-free determination of a value of at least one blood property according to various embodiments. Vacuum stabilization apparatus 1100 may be implemented in embodiments such as system 100 of FIG. 1, system of FIG.

5, system 700 of FIG. 7, and system 900 of FIG. 9. For system 700 of FIG. 7, two opposing vacuum stabilization apparatuses 1100 may be used, one for each side of the body part.

Vacuum stabilization apparatus 1100 may be implemented as an annulus, where the optical objective 1104 of the respective system is positioned so as to gather light that passes through a central opening of the annulus. The annulus includes multiple vacuum interfaces 1102, that is, locations of lower differential air pressure, such that the vacuum interfaces 1102 temporarily adhere the annulus to a body part by way of an air pressure differential with respect to ambient atmospheric pressure. As such, vacuum stabilization apparatus 1100 avoids the need for optical benches or other vibration attenuation techniques. Instead, vacuum stabilization apparatus 1100 keeps the imaging system in which it is implemented effectively motionless with respect to the body part in which blood is being imaged.

Figure 12:
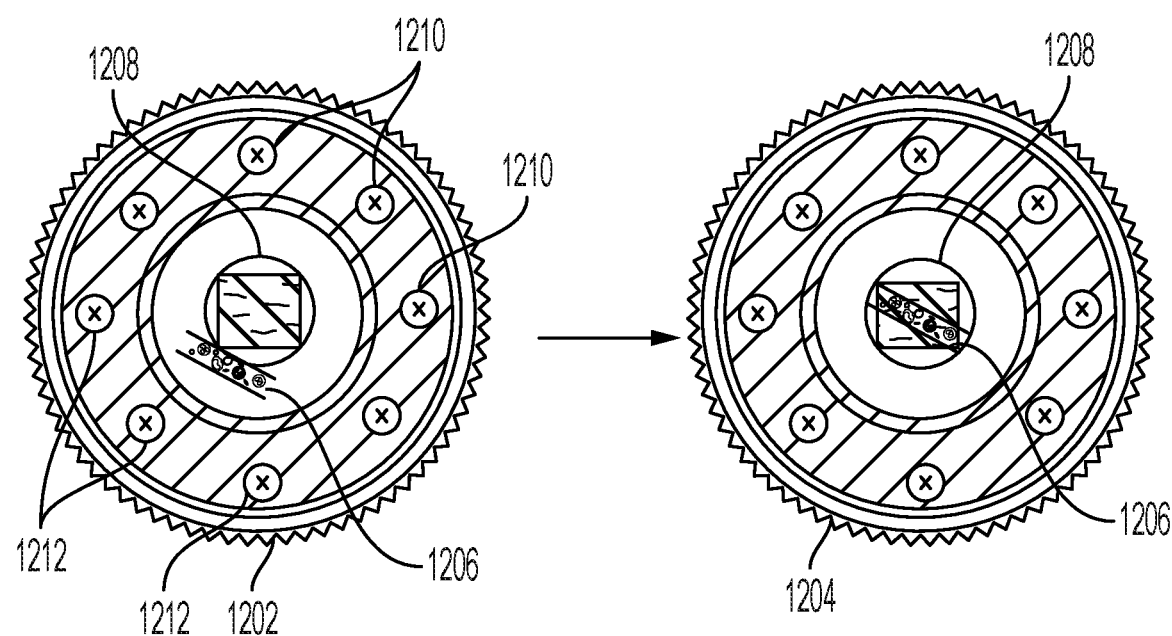
FIG. 12 depicts vacuum positional adjustment of a device for label-free determination of a value of at least one blood property according to various embodiments.

FIG. 12 depicts vacuum positional adjustment of a device for label-free determination of a value of at least one blood property according to various embodiments. In particular, FIG. 12 depicts using vacuum stabilization apparatus 1102 of FIG. 11 to adjust a position of the optical objective's field of view 1208 relative to a capillary 1206 being imaged. As shown, at position 1202, capillary 1206 is outside of field of view 1208. The vacuum interfaces may be used to laterally shift from position 1202 to position 1204, at which capillary 1206 is within field of view 1208. In particular, each vacuum interface may be individually controllable to have a specified air pressure differential relative to the ambient atmospheric pressure. Each vacuum interface (or groups thereof) may have a different such air pressure differential. As depicted in FIG. 12, to adjust the position of vacuum stabilization apparatus 1102 relative to capillary 1206, vacuum interfaces 1210 may have a higher pressure differential (i.e., lower pressure) than vacuum interfaces 1212. Such a different pressure differential among the vacuum interfaces may cause the capillary 1206 to shift within field of view 1208.

Figure 13:
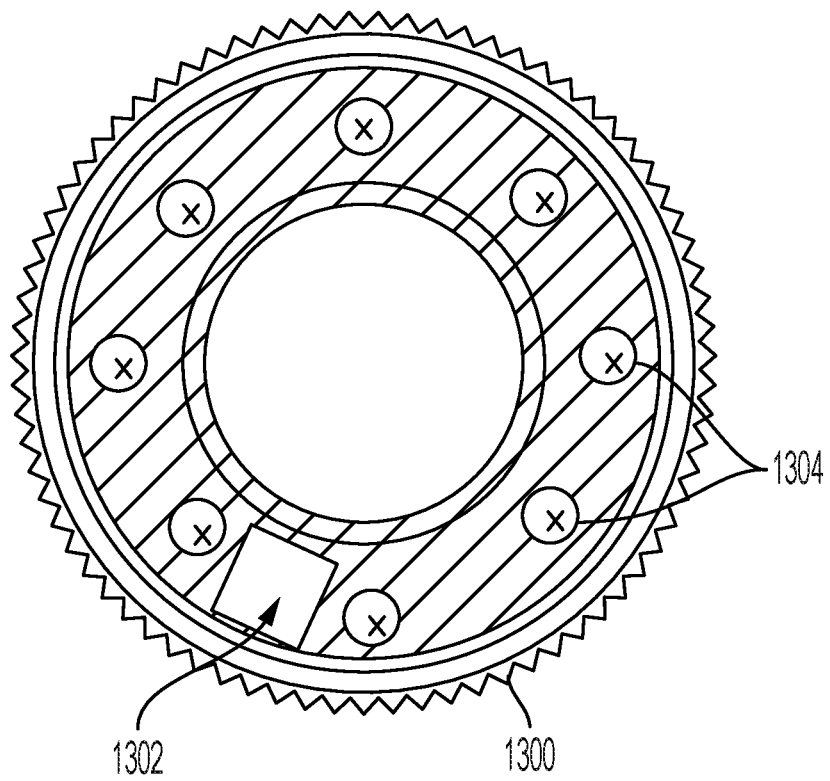
FIG. 13 depicts a temperature sensor on an annulus of a device for label-free determination of a value of at least one blood property according to various embodiments.

FIG. 13 depicts a temperature sensor 1302 on an annulus 1300 of a device for label-free determination of a value of at least one blood property according to various embodiments. Annulus may be an embodiment of annulus 1100 of FIG. 11, including vacuum interfaces 1304 in order to temporarily adhere to a body part. When adhered, temperature sensor 1302, e.g., a thermocouple, contacts the body part and achieves thermal equilibrium. Temperature sensor 1304 may be communicatively coupled to a processor to determine a temperature corresponding to a signal received from temperature sensor 1304. The device in which annulus 1300 is included may display the temperature, adding to the amount of diagnostic information available from the device.

Figure 14:
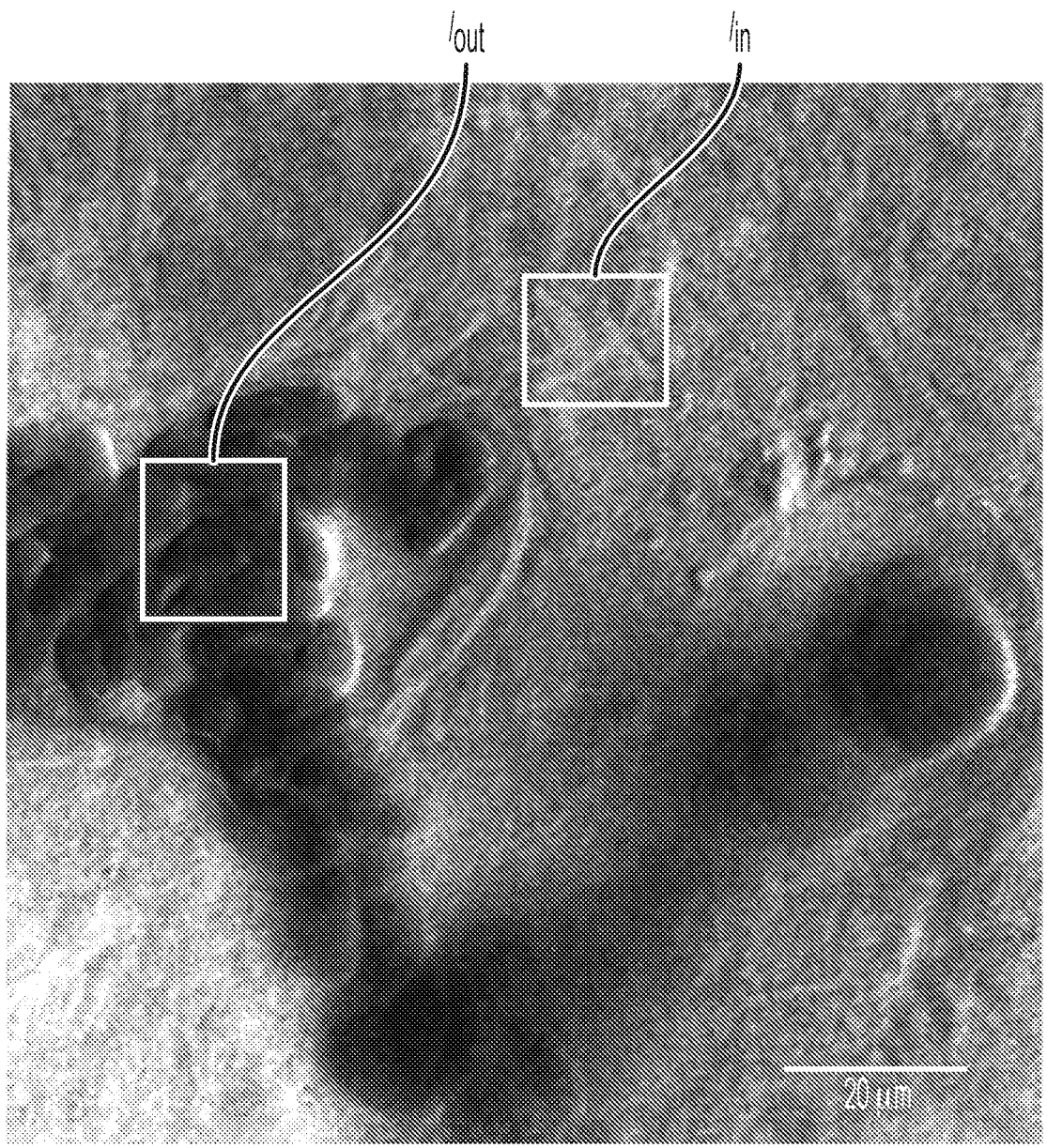
FIG. 14 depicts parameters used for blood oxygenation determination by a device for label-free determination of a value of at least one blood property according to various embodiments.

FIG. 14 depicts parameters used for blood oxygenation determination by a device for label-free determination of a value of at least one blood property according to various embodiments. As shown in FIG. 14, $I_{out}$ represents the intensity of light (units of pixel counts) that is measured for light passing through red blood cells and being absorbed, and $I_{in}$ represents the intensity of incident light (units of pixel counts) being back-scattered from surrounding tissue. Embodiments that determine blood oxygenation may utilize illumination by two light sources, with respective wavelengths $\lambda_1$ and $\lambda_2$, e.g., as shown and described herein in reference to FIG. 5. The following equations may be used to determine blood oxygenation saturation, denoted $SO_2$. In Equation (1), $\epsilon$ represents the molar extinction coefficient of hemoglobin, $\lambda$ represents the wavelength of light, c represents the hemoglobin concentration, and d represents the path length through absorbing blood cells. In Equation (2), OD represents the optical density and the remaining terms are as described above in reference to Equation (1). In Equation (3), $\epsilon_{HbR}$ represents the molar extinction coefficient of de-oxygenated hemoglobin, and the remaining terms are as described above in reference to Equations (1) and (2). In Equation (4), $\epsilon_{HbO_2}$ represents the molar extinction coefficient of oxygenated hemoglobin, and the remaining terms are as described above in reference to Equations (1), (2), and (3).

$$I_{out} = I_{in}\exp[-\epsilon(\lambda)*c*d] \quad (1)$$

$$OD(\lambda) = -\log\left(\frac{I_{out}(\lambda)}{I_{in}(\lambda)}\right) \quad (2)$$

$$SO_2 = \frac{OD(\lambda_2)*\epsilon_{HbR}(\lambda_1) - OD(\lambda_1)*\epsilon_{HbR}(\lambda_2)}{OD(\lambda_1)*\Delta\lambda_2 - OD(\lambda_2)*\Delta\lambda_1} \quad (3)$$

$$\Delta\lambda_n = \epsilon_{HbO_2}(\lambda_n) - \epsilon_{HbR}(\lambda_n), \text{ for } n = 1, 2 \quad (4)$$

Some embodiments may implement any, or a combination, of Equations (1), (2), (3), and (4) in order to determine blood oxygenation saturation, $SO_2$, from parameters $OD(\lambda_n)$, $\epsilon_{HbR}(\lambda_n)$, and $\Delta\lambda_n$ which may be detected using an embodiment.

Figure 15:
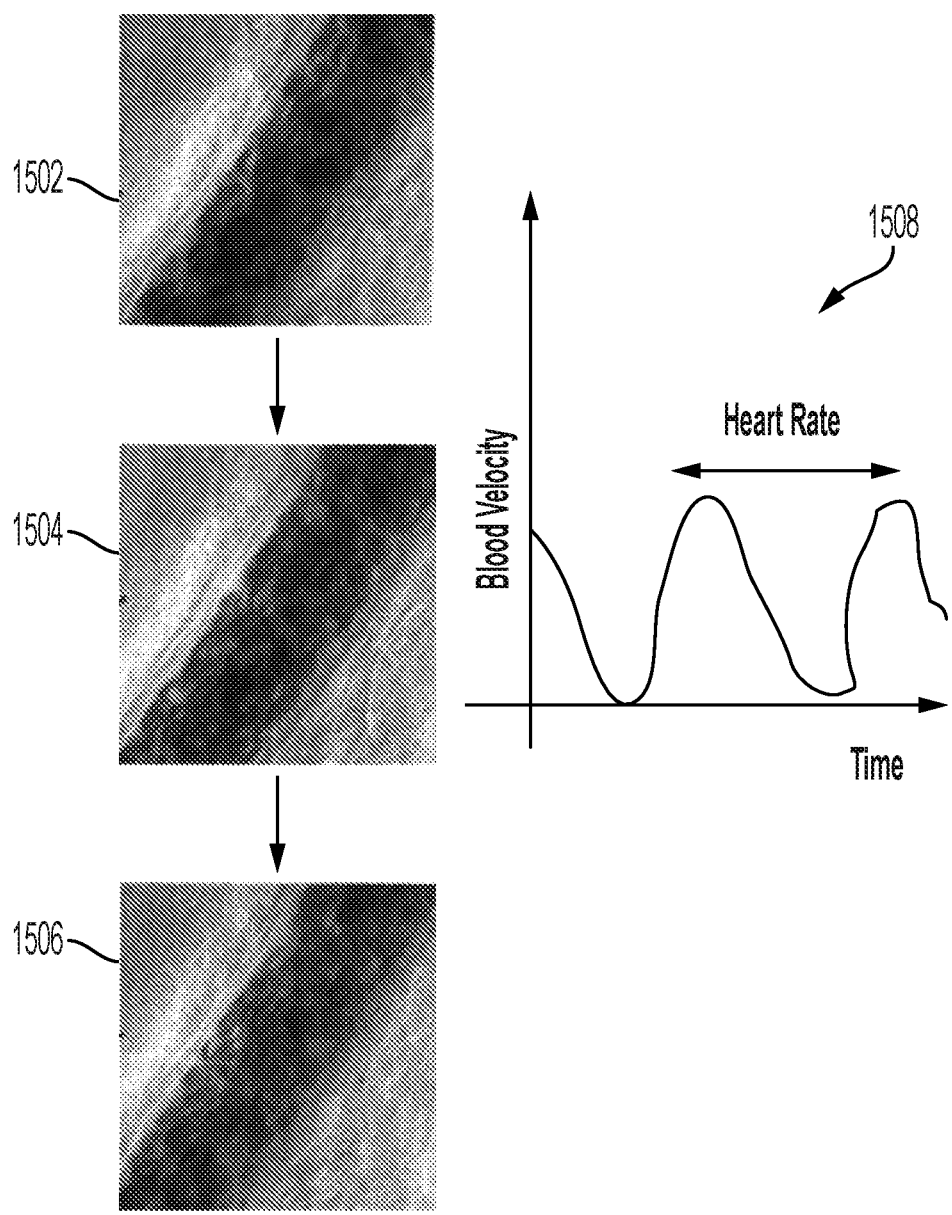
FIG. 15 is a schematic diagram depicting heart rate determination by device for label-free determination of a value of at least one blood property according to various embodiments.

FIG. 15 is a schematic diagram depicting heart rate determination by a device for label-free determination of a value of at least one blood property according to various embodiments. Such a determination may be made by any of the systems for label-free determination of a value of at least one blood property as disclosed herein. To determine heart rate, the device may capture a sequence of images, e.g., images 1502, 1504, 1006, in short temporal succession (e.g., 20 images in less than two seconds). The device may then use image registration techniques to determine how far a particular portion of blood cells have travelled between image captures, thereby estimating blood velocity between such captures. Graph 1508 depicts typical blood velocity as a function of time. Multiple blood velocity captures may be fitted to a curve such as illustrated in graph 1508, and the temporal distance between peaks measured, which provides a heart rate measurement. The device may display the determined heart rate to a clinician, e.g., on a display such as an organic light emitting diode ("OLED") display screen.

Figure 16:
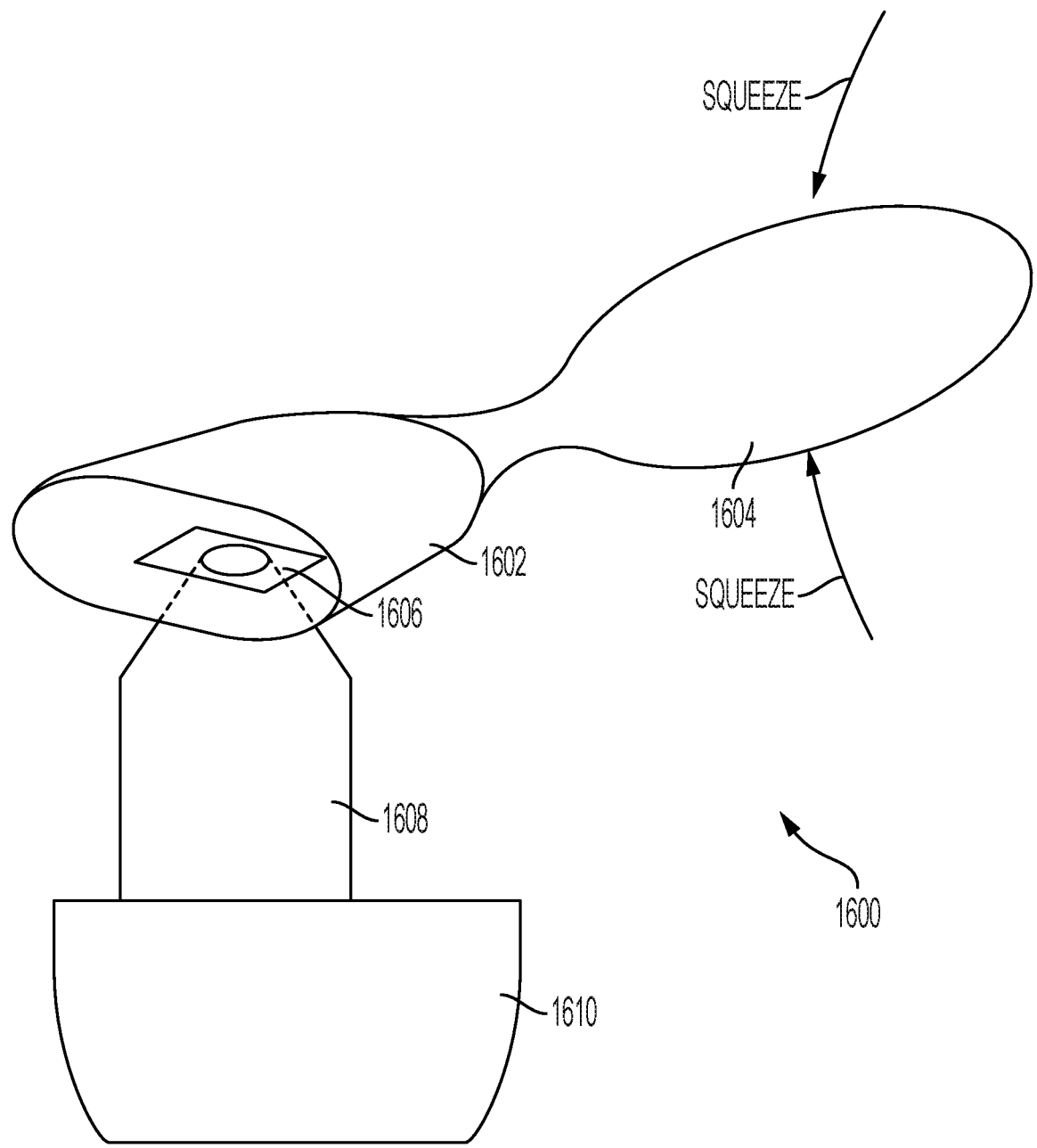
FIG. 16 depicts a variant of a vacuum stabilization apparatus for a device for label-free determination of a value of at least one blood property according to various embodiments.

FIG. 16 depicts a variant of a vacuum stabilization apparatus 1600 for a device for label-free determination of a value of at least one blood property according to various embodiments. As shown, vacuum stabilization apparatus 1600 includes chamber 1602 configured and dimensioned to hold a human tongue. Chamber 1602 includes transparent window 1606, through which an image may be obtained using optical objective 1608. Note that window 1606 may be translucent, as long as the relevant wavelengths may pass through with acceptable diminishment. Chamber 1604 is coupled to vacuum bulb 1604, which may be manually squeezed and released to generate a pressure differential between chamber 1602 and the ambient atmosphere. Optical objective 1608 is coupled to detectors and electronics 1610, which may implement label-free determination of a value of at least one blood property as disclosed herein. Thus, a medical technician may administer a test by squeezing vacuum bulb 1604, placing chamber 1602 about a patient's tongue, releasing vacuum bulb 1604 such that the patient's tongue is received into chamber 1602, and activating the electronics for implement label-free determination of a value of at least one blood property.

Certain embodiments can be performed using a computer program or set of programs. The computer programs can exist in a variety of forms both active and inactive. For example, the computer programs can exist as software program(s) comprised of program instructions in source code, object code, executable code or other formats, firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A system for label-free determination of a value of at least one blood property, the system comprising:
    an optical objective comprising at least one lens;
    at least a first light source situated so as to provide light to a body part at a location that is off-center from a central axis of the optical objective;
    a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror;
    at least a first electronic detector situated to receive light gathered by the optical objective and generate image data;
    at least one electronic processor communicatively coupled to the first electronic detector, the at least one electronic processor configured to determine the value of the at least one blood property based at least in part on the image data; and
    an output interface communicatively coupled to the at least one electronic processor and configured to provide the value of the at least one blood property.

2. The system of claim 1, wherein the at least one blood property comprises a rate of change of a quantifiable blood property.

3. The system of claim 1, wherein the at least one blood property comprises a count of, or ratio comprising, of at least one of: red blood cells, platelets, lymphocytes, neutrophils, lymphocytes, monocytes, eosinophils, or basophils.

4. The system of claim 1, wherein the at least one blood property comprises at least one of: heart rate or blood oxygenation.

5. The system of claim 1, further comprising a machine learning classifier trained to identify in the digital image at least one of: red blood cells, platelets, lymphocytes, neutrophils, lymphocytes, monocytes, eosinophils, or basophils.

6. The system of claim 1, wherein the body part comprises a lingual frenulum.

7. The system of claim 1, wherein the at least a first light source is situated to provide light to the body part through the objective.

8. The system of claim 1, further comprising an annulus comprising at least two vacuum interfaces configured to adhere the annulus to the body part using at least one air pressure differential, wherein the optical objective is situated so as to gather light from the body part through a central opening of the annulus.

9. The system of claim 8, further comprising a temperature sensor situated on the annulus and communicatively coupled to the at least one electronic processor, wherein the at least one electronic processor is further configured to determine a temperature from a signal received from the temperature sensor.

10. The system of claim 8, wherein the at least two vacuum interfaces are configured to adjust a lateral position of the annulus on the body part by applying different air pressure differentials to different vacuum interfaces.

11. A method of label-free determination of a value of at least one blood property, the method comprising:
    applying a device to a body part of a patient, the device comprising:
        an optical objective comprising at least one lens;
        at least a first light source situated so as to provide light to the body part at a location that is off-center from a central axis of the optical objective;
        a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror;
        at least a first electronic detector situated to receive light gathered by the optical objective and generate image data;
        at least one electronic processor communicatively coupled to the first electronic detector, the at least one electronic processor configured to determine the value of the at least one blood property based at least in part on the image data; and
        an output interface communicatively coupled to the at least one electronic processor and configured to provide the value of the at least one blood property; and
    obtaining a reading from the output interface, the reading indicating the value of the at least one blood property.

12. The method of claim 11, wherein the at least one blood property comprises a rate of change of a quantifiable blood property.

13. The method of claim 11, wherein the at least one blood property comprises a count of, or ratio comprising, of at least one of: red blood cells, platelets, lymphocytes, neutrophils, lymphocytes, monocytes, eosinophils, or basophils.

14. The method of claim 11, wherein the at least one blood property comprises at least one of: heart rate or blood oxygenation.

15. The method of claim 11, wherein the device further comprises a machine learning classifier trained to identify in the digital image at least one of: red blood cells, platelets, lymphocytes, neutrophils, lymphocytes, monocytes, eosinophils, or basophils.

16. The method of claim 11, wherein the body part comprises a lingual frenulum.

17. The method of claim 11, wherein the at least a first light source is situated to provide light to the body part through the objective.

18. The method of claim 11, wherein the device further comprises comprising an annulus comprising at least two vacuum interfaces configured to adhere the annulus to the body part using at least one air pressure differential, wherein the optical objective is situated so as to gather light from the body part through a central opening of the annulus.

19. The method of claim 18, wherein the device further comprises a temperature sensor situated on the annulus and communicatively coupled to the at least one electronic processor, wherein the at least one electronic processor is further configured to determine a temperature from a signal received from the temperature sensor.

20. The method of claim 18, wherein the at least two vacuum interfaces are configured to adjust a lateral position of the annulus on the body part by applying different air pressure differentials to different vacuum interfaces.

21. A system for label-free determination of a value of at least one blood property, the system comprising:
    an optical objective comprising at least one lens;
    at least a first light source situated so as to provide light to a body part at a location that is off-center from a central axis of the optical objective;
    an annulus comprising at least two vacuum interfaces configured to adhere the annulus to the body part using at least one air pressure differential, wherein the optical objective is situated so as to gather light from the body part through a central opening of the annulus;
    at least a first electronic detector situated to receive light gathered by the optical objective and generate image data;
    at least one electronic processor communicatively coupled to the first electronic detector, the at least one electronic processor configured to determine the value of the at least one blood property based at least in part on the image data; and
    an output interface communicatively coupled to the at least one electronic processor and configured to provide the value of the at least one blood property.

22. The system of claim 21, further comprising a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror.

23. The system of claim 21, wherein the at least one blood property comprises a rate of change of a quantifiable blood property.

24. The system of claim 21, wherein the at least one blood property comprises a count of, or ratio comprising, of at least one of: red blood cells, platelets, lymphocytes, neutrophils, lymphocytes, monocytes, eosinophils, or basophils.

25. The system of claim 21, wherein the at least one blood property comprises at least one of: heart rate or blood oxygenation.

26. The system of claim 21, further comprising a machine learning classifier trained to identify in the digital image at least one of: red blood cells, platelets, lymphocytes, neutrophils, lymphocytes, monocytes, eosinophils, or basophils.

27. The system of claim 21, wherein the body part comprises a lingual frenulum.

28. The system of claim 21, wherein the at least a first light source is situated to provide light to the body part through the objective.

29. The system of claim 21, further comprising a temperature sensor situated on the annulus and communicatively coupled to the at least one electronic processor, wherein the at least one electronic processor is further configured to determine a temperature from a signal received from the temperature sensor.

30. The system of claim 21, wherein the at least two vacuum interfaces are configured to adjust a lateral position of the annulus on the body part by applying different air pressure differentials to different vacuum interfaces.

31. A method of label-free determination of a value of at least one blood property, the method comprising:
    applying a device to a body part of a patient, the device comprising:
        an optical objective comprising at least one lens;
        at least a first light source situated so as to provide light to the body part at a location that is off-center from a central axis of the optical objective;
        an annulus comprising at least two vacuum interfaces configured to adhere the annulus to the body part using at least one air pressure differential, wherein the optical objective is situated so as to gather light from the body part through a central opening of the annulus;
        at least a first electronic detector situated to receive light gathered by the optical objective and generate image data;
        at least one electronic processor communicatively coupled to the first electronic detector, the at least one electronic processor configured to determine the value of the at least one blood property based at least in part on the image data; and
        an output interface communicatively coupled to the at least one electronic processor and configured to provide the value of the at least one blood property; and
    obtaining a reading from the output interface, the reading indicating the value of the at least one blood property.

32. The method of claim 31, wherein the device further comprises a second light source situated to provide light to the body part at a location that is off-center from the central axis of the optical objective, wherein a wavelength of the first light source is different from a wavelength of the second light source by an amount sufficient for light produced by the first light source and light produced by the second light source to be split by a dichroic mirror.

33. The method of claim 31, wherein the at least one blood property comprises a rate of change of a quantifiable blood property.

34. The method of claim 31, wherein the at least one blood property comprises a count of, or ratio comprising, of at least one of: red blood cells, platelets, lymphocytes, neutrophils, lymphocytes, monocytes, eosinophils, or basophils.

35. The method of claim 31, wherein the at least one blood property comprises at least one of: heart rate or blood oxygenation.

36. The method of claim 31, wherein the device further comprises a machine learning classifier trained to identify in the digital image at least one of: red blood cells, platelets, lymphocytes, neutrophils, lymphocytes, monocytes, eosinophils, or basophils.

37. The method of claim 31, wherein the body part comprises a lingual frenulum.

38. The method of claim 31, wherein the at least a first light source is situated to provide light to the body part through the objective.

39. The method of claim 31, wherein the device further comprises a temperature sensor situated on the annulus and communicatively coupled to the at least one electronic processor, wherein the at least one electronic processor is further configured to determine a temperature from a signal received from the temperature sensor.

40. The method of claim 31, wherein the at least two vacuum interfaces are configured to adjust a lateral position of the annulus on the body part by applying different air pressure differentials to different vacuum interfaces.

* * * * *